United States Patent [19]

Yoshida et al.

[11] 4,150,110

[45] Apr. 17, 1979

[54] COATED GRANULES OF POLYACRYLIC ALKALI METAL SALTS AND METHOD OF PRODUCING SAME

[75] Inventors: Koichi Yoshida, Soka; Hiroshi Ninomiya, Sayama; Fumihiro Sato, Tokyo; Yasuo Ishii, Kashiwa; Yuichi Fujii, Tokyo, all of Japan

[73] Assignee: Nippon Kayaku Kabushiki Kaisha, Tokyo, Japan

[21] Appl. No.: 796,021

[22] Filed: May 11, 1977

[30] Foreign Application Priority Data

May 14, 1976 [JP] Japan .................................. 51-54335

[51] Int. Cl.$^2$ ........................ A61K 9/30; A61K 31/78
[52] U.S. Cl. ........................................ 424/33; 424/81
[58] Field of Search ................................. 424/33, 81

[56] References Cited

U.S. PATENT DOCUMENTS

| | | | |
|---|---|---|---|
| 3,073,748 | 1/1963 | Utsumi et al. | 424/33 |
| 3,576,760 | 4/1971 | Gould et al. | 424/33 |
| 3,577,512 | 5/1971 | Shepherd et al. | 424/33 |
| 3,900,559 | 8/1975 | Sim et al. | 424/81 |
| 3,901,968 | 8/1975 | Cohen et al. | 424/81 |
| 3,901,969 | 8/1975 | Cohen et al. | 424/81 |
| 3,901,971 | 8/1975 | Cohen et al. | 424/81 |

FOREIGN PATENT DOCUMENTS

| | | | |
|---|---|---|---|
| 927976 | 6/1963 | France | 424/33 |
| 39-17534 | 8/1964 | Japan | 424/33 |

*Primary Examiner*—Delbert R. Phillips
*Attorney, Agent, or Firm*—Russell & Nields

[57] ABSTRACT

Granules of polyacrylic alkali metal salts are coated with a water-insoluble but water-permeable coating agent.

6 Claims, No Drawings

COATED GRANULES OF POLYACRYLIC ALKALI METAL SALTS AND METHOD OF PRODUCING SAME

BACKGROUND OF THE INVENTION

It is known that polyacrylic alkali metal salts have a prominent remedial effect against peptic ulcers (see for example British Patent No. 1435630). In use of such salts alone for human beings, it is hardly possible to administer them orally in the form of powder because of their too strong adhesive nature. Also, even if they could be administered, they are likely to form an undissolved lump in the stomach and can hardly spread and adhere sufficiently to the mucous membranes of the stomach and duodenum, so that such salt substance must be given at a high dose for inducing a significant effect. Therefore, it is more preferable to give said salt substance in a form dissolved in water, but actually, this mode of administration is impractical because more than 20 hours are required for this substance to get dissolved uniformly in water.

There is also known an easily water-soluble granular polyacrylic alkali metal salt preparation obtained by contacting powder of a polyacrylic alkali metal salt with water in a hydrophilic organic solvent, crushing the obtained masses into aggregated granules of desired size (aggregates of primary particles of polyacrylic alkali metal salt), and then coating the granules with a water-soluble polyethylene glycol or a polyoxyethylene derivative which is solid at normal temperature, or with a mixture thereof and a higher fatty acid which is solid at normal temperature, or with such higher fatty acid alone (Japanese Patent Laid-Open No. 133251/75). However, this granular preparation has a drawback in its use as a digestive ulcer remedial medicament as it needs to use the coating agent in an amount of more than 20% of the amount of the base polyacrylic alkali metal salt because otherwise the granules, when administered, could cling to each other to form undissolved lumps, resulting in reduced solubility of the substance in the stomach or duodenum.

In view of the above, the present inventors have devoted themselves to the study for working out a medicinal preparation of polyacrylic alkali metal salts which can produce a high remedial effect against digestive ulcers and which is easy to administer and can be also produced on a commercial scale, and as a result, it was found quite unexpectedly that if such polyacrylic alkali metal salt substance is first granulated according to a proper method and then the obtained granules are coated with a water-insoluble but water-permeable coating agent, said granules when contacted with water, are quickly swollen and dissolved in water to form a uniform viscous solution, allowing easy obtainment of the desired coated granules. This discovery breaks away from the conventional conception that use of an easily water-soluble coating agent is essential for obtaining water-soluble granules.

SUMMARY OF THE INVENTION

This invention was completed on the basis of the above-described discovery, and it relates to a coated granule characterized in that the granules of a polyacrylic alkali metal salt are coated with a water-insoluble but water-permeable coating agent.

DESCRIPTION OF THE PREFERRED EMBODIMENTS

The polyacrylic alkali metal salts used in this invention include, for example, sodium salt and potassium salt of polyacrylic acid with molecular weight of about 3,000,000 to 8,000,000 and particle size of 16 to 100 mesh (Tyler).

The granules used for this invention may be: (a) those obtained by contacting powder of a polyacrylic alkali metal salt in a hydrophilic organic solvent to let the powder swell and aggregate, then after removal of the solvent, drying the aggregates and crushing the obtained dry masses into granules, as described in the afore-mentioned Japanese Patent Laid-Open No. 133251/75; (b) those obtained by polymerizing an acrylic alkali metal salt to form a gel-like mass, then subjecting the mass to an extrusion granulator and drying the obtained granules; (c) those obtained by drying a gel of a polyacrylic alkali metal salt in the form of a mass and crushing this mass into coarse granules; (d) those obtained by kneading powder of a polyacrylic alkali metal salt with a suitable organic solvent such as methanol, ethanol or chloroform with or without addition of a suitable bulk filler such as lactose, mannitol or starch and/or a binder such as polyvinyl pyrrolidone or methyl cellulose, and granulating the mixed mass by a granulator, and (e) those obtained by granulating a prepared mass of a polyacrylic alkali metal salt with a fluidized bed granulator-dried by using a water-soluble or water-insoluble high molecular weight substance as binder.

The water-insoluble but water-permeable coating agents usable in this invention for coating of the granules such as above-mentioned include the following: copolymer of acrylic acid, methacrylic acid and vinylpyridine, ethyl cellulose, polyvinyl acetal diethylaminoacetate, copolymer of dimethylaminoethyl methacrylate and methacrylate ester, cellulose acetate phthalate, hydroxypropyl cellulose phthalate, polyvinyl acetate, cellulose acetate, shellac and zein. If need be, a glycerin fatty acid such as triacetin, myvacet ® (trademark for glycerin monoaliphatic diacetic ester, manufactured Eastman Kodak) and other fats and oils may be added as plasticizer to the coating agent. It is also possible to add a coloring matter, sweetening agent or smell-drowning agent without inviting any detrimental effect.

For preparing the water-insoluble but water-permeable coated granules according to this invention, one or more of the above-mentioned coating agents is dissolved in one or a mixture of two or more of the suitable solvents such as ethanol, isopropyl alcohol, methylene chloride, chlorothen, acetone, etc., by adding, if need be, a plasticizer such as above-mentioned and further adding, if necessary, a coloring matter and/or other additives also mentioned above, and applying this coating solution to the granules by using, for example, a fluidized bed coating machine or a rolling coater.

The thus obtained coated granules may be additionally coated with another coating agent with relatively high viscosity such as hydroxypropyl cellulose to make the granular medicine pleasant to take.

The coating on each granule should be less than 15%, preferably 2 to 10% by weight, of the granule. As apparent from the results of experiments and embodiments of this invention, these coated granules show an excellent anti-peptic-ulcer activity and good solubility in water.

In use of the coated granules of this invention for human beings, they may be administered either in the form as they are or in admixture with bulking granules prepared by using a bulk filler such as lactose, mannitol or starch and a binder such as polyvinyl pyrrolidone. In the latter case, the optimum dose should be determined depending on the filler loadings.

The prominent medicinal effect of the water-insoluble but water-permeable coated granules according to this invention is described below by way of the results of an experiment which follows.

Experiment: Effect on experimental ulcers formed on rats by subcutaneous injection of cysteamine hydrochloride and time required for dissolution (1) Specimens Specimen A: 50- to 250-mesh powder of sodium polyacrylate with average molecular weight of about 3,400,000.

Specimen B: Aggregated granules used in Example 1.

Specimen C: 6% ethyl cellulose coated granules obtained in Example 1.

Specimen D: 4% ethyl cellulose coated granules obtained from a similar treatment to Example 1.

Specimen E: 2% ethyl cellulose coated granules obtained in the same way as Example 1.

Specimen F: 20- to 65-mesh 3% polyethylene glycol coated granules obtained by adding 97 parts of specimen B to 3 parts of molten polyethylene glycol, mixing them in a small-sized universal mixer, cooling and solidifying the mixture, and subjecting the agglomerate of the obtained granules to forced screening to obtain the granules of the specified range of granule size, according to the method described in Japanese Patent Laid-Open No. 133251/75.

Specimen G: 6% polyethylene glycol coated granules obtained from the same treatment as specimen F.

Specimen H: 9% polyethylene glycol coated granules obtained in the same way as specimen F.

Specimen I: 20% polyethylene glycol coated granules obtained after the manner of specimen F.

Specimen J: Extrusion-granulated granules used in Example 3.

Specimen K: 4% ethyl cellulose coated granules obtained by treating specimen J after the pattern of Example 1.

Specimen L: 6% ethyl cellulose coated granules obtained by treating specimen J after the pattern of Example 1.

Specimen M: Coarse granules used in Example 4.

Specimen N: 4% ethyl cellulose coated granules obtained by treating specimen M after the mode of Example 1.

Specimen O: 6% ethyl cellulose coated granules obtained by treating specimen M similarly to Example 1.

Specimen P: 25% aqueous solution of sodium carboxymethyl cellulose (CMC Na) (300 cp).

Specimen Q: 25% aqueous solution of sodium amylopectin sulfate (APS).

(2) Method of experiment (a) Anti-ulcer test

Male Wistar rats (weighing 220 gr on the average) were fasted for 24 hours and then 400 mg/Kg of cysteamine hydrochloride was given to them subcutaneously. 18 hours after cysteamine administration, they were killed and the ulcer area ($mm^2$) in each rat was measured by a stereomicroscope ($\times 10$), with such ulcer area being given as ulcer index.

Each specimen was suspended in distilled water such that the specimen concentration calculated as sodium polyacrylate would become 1.25%, and 250 mg/kg (20 ml/kg) of each such treated specimen (just prepared) was administered orally to each rat immediately before giving cysteamine. CMC Na and APS were also similarly administered at the dose of 500 mg/kg. The results are shown in the table given below.

(b) Dissolving speed

Test: 2 parts of each specimen and 30 parts of water were quickly and simultaneously put into a cylinder and change of viscosity of the mixture with time was measured at 37° C. by using Tokyo Keiki's Model R Viscometer Spindle No. 4. In this test, the time required for reaching viscosity of 8,000 cp was determined as a measure of the dissolution and diffusion rate, and this was expressed as dissolution time (sec.) in the following table.

(3) Results of experiment

The results of the experiment are as shown in the following table.

|  | Specimen | Coating (%) | Nr. of rats tested | Ulcer index ($mm^2$) and inhibitory effect (%) | Dissolution time (sec) |
|---|---|---|---|---|---|
| Coated granules according to this invention | E | 2 | 20 | 15.3 ± 3.4 (43.3) | 117 |
|  | D | 4 | 20 | 10.1 ± 3.1 (62.6) | 98 |
|  | C | 6 | 20 | 7.5 ± 2.6 (72.2) | 72 |
|  | K | 4 | 20 | 15.5 ± 3.1 (42.6) | 122 |
|  | L | 6 | 20 | 12.5 ± 2.8 (53.7) | 96 |
|  | N | 4 | 20 | 13.0 ± 2.6 (51.9) | 112 |
|  | O | 6 | 20 | 8.6 ± 2.9 (68.1) | 77 |
| *Coated granules according to a known method | F | 3 | 20 | 17.4 ± 2.5 (35.6) | 138 |
|  | G | 6 | 20 | 18.1 ± 3.1 (33.0) | 142 |
|  | H | 9 | 20 | 16.1 ± 2.4 (40.4) | 130 |
|  | I | 20 | 20 | 13.5 ± 2.3 (50.0) | 110 |
| Non-coated granules and powder | A | — | 20 | 20.2 ± 2.4 (25.2) | 750 |
|  | B | — | 20 | 17.0 ± 3.8 (37.0) | 143 |
|  | J | — | 20 | 18.5 ± 3.9 (31.5) | 205 |
|  | M | — | 20 | 20.6 ± 2.1 (23.7) | 184 |
| Others | P | — | 20 | 27.3 ± 6.0 (−1.1) | — |
|  | Q | — | 20 | 25.2 ± 4.4 (6.7) | — |
| Control |  | — | 40 | 27.0 ± 2.8 (—) | — |

*Japanese Patent Laid-Open No. 133251/75

It is noted from the above table that the coated granular preparations according to this invention are superior to those obtained from a known method in ulcer index ($mm^2$), inhibitory effect (%) and dissolution time, that they are by far superior to the non-coated preparations or powder, and that a particularly salient effect is given by the 6% ethyl cellulose coated aggregated granules (specimen C), similar 4% ethyl cellulose coated granules (specimen D), extrusion-granulated 6% ethyl cellulose coated granules (specimen L) and coarse 6% ethyl cellulose coated granules (specimen O).

It is also noted that proper increase of the coating thickness leads to increased dissolution rate and also proves helpful to perfectly inhibit formation of undissolved lumps which are seen in the case of powder of polyacrylic alkali metal salts or non-coated granules. This is considered conducive to the effective action of the polyacrylic alkali metal salts to the ulcer.

CMC Na (viscous material) and APS (antipepsin agent) also tested for the sake of reference produced no significant effect.

For use of the polyacrylic alkali metal salts granules coated with a water-insoluble but water-permeable coating agent according to this invention as a peptic ulcer remedial medicament, it is recommended to give the perparation four times a day at the dose of 500 to 1000 mg based on the polyacrylic alkali metal salt for adult.

Now, preparation of the water-insoluble and water-permeable coated granules according to this invention is described by way of some embodiments thereof.

EXAMPLE 1

15 kg of aggregated granules were supplied into a fluidized bed coating machine (a product by Gratt Co., West Germany) and they were coated with a coating solution consisting of 5 parts of ethyl cellulose (10 cp), 1 part of glycerin fatty acid ester (a product by Nisshin Seiyu Co., Ltd.), 47 parts of methanol and 47 parts of methylene chloride until a weight increment of 900 gr based on solids content was attained, and then the coated granules were subjected to a 20-mesh screen to obtain 15.9 Kg of regularly sized coated granules.

The dissolution time of the thus obtained granules was 72 seconds and the ulcer index as determined by an experimental ulcer curing test on rats (using 20 rats and administering the granules orally at the dose of 250 mg/kg) was $7.5 \pm 2.6$ $mm^2$.

The aggregated granules used as base material in this example were made in the following way. 7 kg of powder (50 to 100 mesh) of sodium polyacrylate with average molecular weight of about 3,400,000 is added gradually under agitation into a 50-litre butt containing 35 kg of 25% hydrous ethanol (V/V), and after agitating the mixture for 5 minutes, it is allowed to stand still for one hour. Thereafter, the solvent is removed as much as possible and the residue is added with 14 kg of anhydrous ethanol and allowed to stand for 30 minutes with agitation from time to time. Then the solvent is filtered off and the obtained aggregates of primary particles are dried in a dryer at 80° to 90° C. for 16 hours, and the dried aggregates are broken down by a granulator into granules and the latter are subjected to a 20 to 80 mesh screen to obtain 6.2 kg of granules with the required size range.

EXAMPLE 2

The coated granules obtained in Example 1 were further coated with a coating solution consisting of 5 parts of hydroxypropyl methyl cellulose (a product by Shinetsu Kagaku Co., Ltd.), 1 part of propylene glycol, 47 parts of methanol and 47 parts of methylene chloride in the same way as Example 1. Coating was ended at a point where a weight increment of 300 gr to total 7.95 kg of coated granules of Example 1 was attained, and the thus coated granules were subjected to a 20 mesh screen to obtain the regularly sized coated granules.

The dissolution time of these granules was 85 seconds and the ulcer index was $7.8 \pm 2.6$ $mm^2$.

EXAMPLE 3

15 kg of extrusion-granulated granules were coated after the manner of Example 1 with a coating solution consisting of 5 parts of an acrylic acid, methacrylic acid and vinylpyridine copolymer (a product by Tanabe Seiyaku Co., Ltd.), 1 part of triacetin, 47 parts of methanol and 47 parts of methylene chloride, with the coating being ended at a point where a 1.5 kg weight increment based on solids content was achieved, and the thus coated granules were subjected to a 20-mesh screen to obtain 16.5 kg of coated granules with regulated sizes.

The dissolution time of the thus obtained granules was 78 seconds and the ulcer index was $9.3 \pm 2.7$ $mm^2$.

The granules used as base material in this example were prepared in the following way. 50 parts of sodium polyacrylate (less than 200 mesh) with average molecular weight of about 3,400,000, 4 parts of polyvinyl pyrrolidone and 46 parts of mannitol are mixed well in the powdery form. Then the mixture is further added with 30 parts of methanol and, after well kneading the entire mixture, it is granulated with an extrusion granulator by using a 7 mm-diameter screen, then dried and passed through a sieve to obtain 97 parts of granules of 20 to 80 mesh.

EXAMPLE 4

15 kg of coarse granules (20 to 48 mesh) of sodium polyacrylate with average molecular weight of about 3,800,000 were coated with a coating solution consisting of 5 parts of hydroxypropyl cellulose phthalate (a product by Shinetsu Kagaku Co., Ltd.), 1 part of refined sesame oil, 47 parts of acetone and 47 parts of methylene chloride in the same way as Example 1, with the coating being ended upon attainment of a 1200 gr coating weight increment, and the thus coated granules were passed through a 20-mesh sieve to obtain 16.2 kg of regularly sized coated granules.

The dissolution time of the thus obtained granules was 78 seconds and the ulcer index was $7.8 \pm 2.4$ $mm^2$.

What is claimed is:

1. The process for treating peptic ulcers in humans which comprises internally administering to said humans an effective amount of polyacrylic alkali metal salt granules coated with a water-insoluble but water-permeable coating agent.

2. The process for treating peptic ulcers as claimed in claim 1, wherein the polyacrylic alkali metal salt is sodium salt or potassium salt of polyacrylic acid.

3. The process for treating peptic ulcers as claimed in claim 1, whrein the polyacrylic alkali metal salt has a molecular weight of 3,000,000 to 8,000,000.

4. The process for treating peptic ulcers as claimed in claim 1, wherein the size of the coated granules is 16 to 100 mesh (Tyler).

5. The process for treating peptic ulcers as claimed in claim 1, wherein the water-insoluble but water-permeable coating agent is a material selected from the group consisting of (a) copolymer of acrylic acid, methacrylic acid and vinylpyridine,
(b) copolymer of dimethylaminoethyl methacrylate and methacrylate ester,
(c) ethyl cellulose,
(d) hydroxypropylmethyl cellulose,
(e) hydroxypropyl cellulose phthalate,
(f) cellulose acetate phthalate,
(g) polyvinyl acetal diethylamino acetate,
(h) polyvinyl acetate,
(i) cellulose acetate,
(j) shellac and
(k) zein.

6. The process for treating peptic ulcers as claimed in claim 1, wherein the coating is 2 to 15% by weight of the granule.

* * * * *